United States Patent
Desfougeres et al.

(10) Patent No.: US 9,309,524 B2
(45) Date of Patent: Apr. 12, 2016

(54) METHOD FOR PREPARING AN INDUSTRIAL YEAST, INDUSTRIAL YEAST, AND APPLICATION TO THE PRODUCTION OF ETHANOL FROM AT LEAST ONE PENTOSE

(75) Inventors: Thomas Desfougeres, Neuville en Ferrain (FR); Georges Pignede, Marcq en Baroeul (JP)

(73) Assignee: LESAFFRE ET COMPAGNIE, Paris (FR)

( * ) Notice: Subject to any disclaimer, the term of this patent is extended or adjusted under 35 U.S.C. 154(b) by 123 days.

(21) Appl. No.: 13/310,578

(22) Filed: Dec. 2, 2011

(65) Prior Publication Data

US 2012/0142067 A1 Jun. 7, 2012

(30) Foreign Application Priority Data

Dec. 3, 2010 (FR) ...................................... 10 04709

(51) Int. Cl.
*C12P 7/06* (2006.01)
*C12P 7/10* (2006.01)
*C12N 1/00* (2006.01)
*C12N 15/00* (2006.01)
*C07H 21/04* (2006.01)
*C12N 15/81* (2006.01)
*C12N 1/16* (2006.01)
*C12N 9/04* (2006.01)
*C12N 9/92* (2006.01)
*C12R 1/865* (2006.01)

(52) U.S. Cl.
CPC *C12N 15/81* (2013.01); *C12N 1/16* (2013.01); *C12N 9/0006* (2013.01); *C12N 9/92* (2013.01); *C12P 7/10* (2013.01); *C12R 1/865* (2013.01); *C12Y 101/01009* (2013.01); *C12Y 101/01021* (2013.01); *C12Y 503/01005* (2013.01); *Y02E 50/16* (2013.01); *Y02E 50/17* (2013.01)

(58) Field of Classification Search
None
See application file for complete search history.

(56) References Cited

U.S. PATENT DOCUMENTS 5,866,382 A * 2/1999 Hallborn et al. ............... 435/158
2009/0246844 A1 * 10/2009 Khramtsov et al. ........... 435/161
2010/0291648 A1 11/2010 Alper et al.

FOREIGN PATENT DOCUMENTS

WO WO 2009/109634 A1 9/2009

OTHER PUBLICATIONS

Brat et al. Functional expression of a bacterial xylose isomerase in *Saccharomyces cerevisiae*, Appl and Environ Microbiol (2009, Epub Feb. 13, 20090), 75: 2304-2311.*
Traff et al. Deletion of GRE3 aldose reductase gene and its influence on xylose metabolism in recombinant strains of *Saccharomyces cerevisiae* expressing xylA and XKS1 gene, Appl and Environ Microbiol (2001), 67: 5668-5674.*
Bengtsson, Oskar, et al., "Xylose reductase from Pichia stipitis with altered coenzyme preference improves ethanolic xylose fermentation by recombinant *Saccharomyces cerevisiae*", Biotechnology for Biofuels, 2009, 2:9.
Bettiga, Maurizio, et al., "Comparing the xylose reductase/xylitol dehydrogenase and xylose isomerase pathways in arabinose and xylose fermenting *Saccharomyces cerevisiae* strains", Biotechnology for Biofuels, 2008, 1:16.
Hahn-Hagerdal, Barbel, et al., "Toward industrial pentose-fermenting yeast strains", Appl. Microbiol Biotechnol, (2007) 74:937-953.
Karhumaa, Kaisa, et al., "Investigation of limiting metabolic steps in the utilization of xylose by recombinant *Saccharomyces cerevisiae* using metabolic engineering", Yeast 2005: 22:359-368.
Matsushika, Akinori, et al., "Ethanol production from xylose in engineered *Saccharomyces cerevisiae* strains: current state and perspectives", Appl. Microbiol Biotechnol (2009) 84:37-53.
Van Maris, Antonius J. A., et al., "Development of Efficient Xylose Fermentation in *Saccharomyces cerevisiae*: Xylose Isomerase as a Key Component", Adv. Biochem Engin/Biotechnol, (2007), 108: 179-204.

* cited by examiner

*Primary Examiner* — Iqbal H Chowdhury
(74) *Attorney, Agent, or Firm* — Sughrue Mion, PLLC

(57) ABSTRACT

The present invention relates to methods for obtaining ethanol-producing yeast strains, yeast strains thus produced, and the industrial production of ethanol from said strains. More particularly, the present invention describes in its most general aspect, a method for preparing yeasts from *Saccharomyces cerevisiae* strains by means of the integration, into the genome of the yeast, of at least one gene encoding xylose isomerase and of at least one gene encoding xylitol dehydrogenase. The strains of the invention are useful for producing ethanol from a medium comprising at least one pentose, preferably xylose or a mixture of xylose and arabinose.

30 Claims, 5 Drawing Sheets

METHOD FOR PREPARING AN INDUSTRIAL YEAST, INDUSTRIAL YEAST, AND APPLICATION TO THE PRODUCTION OF ETHANOL FROM AT LEAST ONE PENTOSE

TECHNICAL FIELD

The present invention relates to the field of methods for obtaining yeast strains producing ethanol, to the thereby produced yeasts, and to the industrial production of ethanol from said yeasts. More particularly, the present invention in its most general aspect relates to a method for preparing yeasts from so-called industrial strains of *Saccharomyces cerevisiae*, to said yeasts and their application to the industrial production of ethanol from industrial media containing at least one pentose, notably xylose.

TECHNICAL BACKGROUND

The point in common of most approaches of the prior art of the field consists in methods aiming at improving strains with known genetic heritage and/or constructed genetic heritage and the capabilities of which for producing ethanol are generally studied in media and under <<ideal>> laboratory conditions.

Indeed, scientific literature as well as patent documents analyzed by the Applicant most often teach methods for obtaining haploid or diploid strains, little tolerant to stresses notably to strong concentrations of ethanol and/or to high temperatures and/or to fermentation inhibitors. Further, these methods for the most part require resorting for these strains to the use of auxotrophy markers and/or markers of resistance to antibiotics which may disqualify them for subsequent use in an industrial medium for obvious reasons of cost or even sometimes of health or respect of the environment.

The growth properties of strains developed previously are generally insufficient and these strains have never been confronted with biomass production requirements on an industrial scale, i.e. in order to only mention three of them: strong growth rate, drying capacity, storage stability.

If so-called fermentative performances (anaerobic ethanol production capacity) are obtained in synthetic or defined media, so-called laboratory media with these previous strains, they generally cannot be transposed in industrial media including complex mixtures for example stemming from cellulose-processing residues which contain toxic compounds which may inhibit at different levels the yeast's cell mechanism, notably furfural, HMF, phenolic derivatives, acetic acid. Further, the <<scale up>> or scale transposition capacity of these earlier ethanol production methods is seldom documented.

The document WO 2008/133665 teaches the production of alcohol from a yeast strain with a <<genetic background>> of the type:
  Mutated STP15 gene (F117S, Y195H, K218R).
  Exogenous genes coding for XI/XR/XDH or XK.
  "XI" means xylose isomerase, "XR" means xylose reductase, "XDH" means xylitol dehydrogenase, and "XK" means D-xylulokinase.

Document WO 2005/113774 describes a recombinant operon comprising two nucleic acid sequences respectively coding for an XI of *E. coli* and an XDH of *Trichoderma reesei* in the context of the production of xylitol.

The document PloS Genetics of Gavin Sherlok et al., published on May 13, 2010, describes an XDH1 gene which is present in some specific *Saccharomyces cerevisiae* strains, which may code for a xylitol dehydrogenase.

The document in the name of David Brat, Eckard Boles and Beate Wiedemannn, in Appl. Environ. Microbiol., April 2009, Vol. 75, No. 8, p. 2304-2311, describes the expression of the xylose isomerase gene from *Clostridium phytofermentans* in *Saccharomyces cerevisiae*.

It emerges from this review of the documents of the prior art, as well as of the work of the inventors of the present invention, that given the very different genetic background/ heritages of the strains of *Saccharomyces cerevisiae* yeasts applied with the purpose of growing on and/or fermenting xylose, the consequences for example of overexpression and/ or of deletion of native genes and/or of the introduction of one or more heterologous genes cannot be predicted.

SUMMARY OF THE INVENTION

Also, the Applicant studying many strains of the alcohol, brewery and bakery type, noticed surprisingly that the introduction of determined expression or deletion cassettes in yeast strains so as to express therein a metabolic route XI-XDH made them particularly performing in the production of ethanol. Further, the Applicant noticed that the introduction of nucleic acid coding for XI is not sufficient by itself for efficiently fermenting xylose.

Generally, the Applicant noticed that the introduction of expression cassettes of a gene coding for an enzyme capable of transforming any carbohydrate (notably xylose) into xylulose (D-xylulose) and of a gene coding for an enzyme capable of transforming any pentol (notably xylitol) into xylulose in a single step, made all the thereby modified strains particularly performing in growing on and/or fermenting xylose.

By "enzyme capable of transforming xylose into xylulose", is meant a xylose isomerase enzyme.

By "enzyme capable of transforming xylitol into xylulose in a single step" is meant a xylitol dehydrogenase enzyme.

Indeed, the Applicant confirmed that, unlike the so-called fungal route associating XR and XDH, the so-called bacterial isomerization route (an example of which is that of *C. phytofermentans*) when it is applied does not involve any co-substrates. Further, this route gives the possibility of avoiding accumulation of xylitol which is a metabolic intermediate present in the fungal route and which may significantly reduce the ethanol production yield.

Very recently, on certain *S. cerevisiae* strains, notably those for wine-making, a gene XDH1 was identified as being essential for the metabolism of xylose of said strains (PLoS genetics 2010, 6, 1-17). Also, the Applicant noticed that even by suppressing the GRE3 gene of the modified strains, there exists other parasitic activities which may transform xylose into xylitol (aldose reductase activity), which is detrimental for the XI activity thereby reducing the sought ethanol yield.

The work carried out by the Applicant shows that reinforcement of the xylitol dehydrogenase activity is expressed by the absence of inhibition of XI and therefore by the stimulation of this route, which allows the production of ethanol, from a medium including at least xylose, with a good kinetic yield.

In other terms, in the prior art, two different pathways were explored so as to make the fermentation of xylose by yeast possible: the so-called fungal pathway, which makes use of the XR and XDH enzymes; and the so-called bacterial pathway, which makes use of the XI enzyme. The invention combines the enzymes from both of these pathways in an original manner, so as to obtain an improved result.

The invention is defined in the appended claims.

The invention particularly relates to a yeast strain comprising at least one copy of an exogenous gene coding for a xylose isomerase, and one copy of an exogenous gene coding for a xylitol dehydrogenase.

By "exogenous" gene (as opposed to "endogenous") is meant a gene which is not naturally present in the yeast species at stake. The gene coding for a xylitol dehydrogenase may be a XYL2 gene, but in this case it is an XYL2 gene from another species than that of the strain at stake.

The invention also relates to a method of preparing a yeast strain comprising at least a copy of an exogenous gene coding for a xylose isomerase, and a copy of an exogenous gene coding for a xylitol dehydrogenase.

The invention also relates to a method of producing ethanol using the yeast strains according to the invention.

DETAILED DESCRIPTION OF EMBODIMENTS

Figure 1:
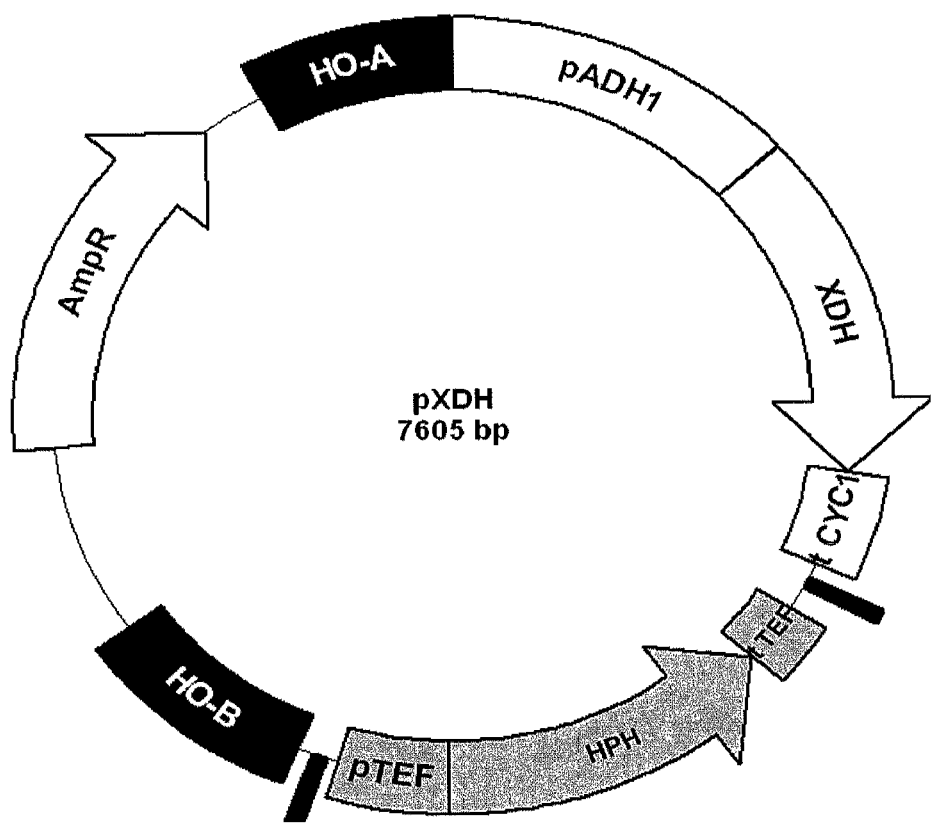
FIG. 1 illustrates an overexpression vector of XDH from *Pichia stipitis*.

Thus, the first object of the present invention is a method for preparing a *Saccharomyces cerevisiae* yeast strain capable of producing ethanol from a medium including at least one pentose (notably xylose) and which comprises the following steps:

(i) selecting (or providing) a *Saccharomyces cerevisiae* yeast strain (ii) integrating the following expression cassettes into the genome of the yeast of step (i), a. the association of the open reading frame (ORF) type of a gene coding for an enzyme capable of transforming any carbohydrate, notably xylose, into xylulose under the dependency of a promoter and of a *Saccharomyces cerevisiae* terminator, said cassette being flanked upstream and downstream with recombinogenic regions allowing its targeted integration into the genome, b. the association of the open reading frame (ORF) type of a gene coding for an enzyme capable of transforming in a single step any pentol, notably xylitol, into xylulose under the dependency of a *Saccharomyces cerevisiae* promoter and terminator, said cassette being flanked upstream and downstream with recombinogenic regions allowing its targeted integration into the genome, (iii) inducing the expression of at least one gene of each step of the non-oxidative portion of the phosphate pentose route as well as of at least one gene coding for xylulokinase (XKS1) by placing them under the dependency of a promoter of a gene, notably a glycolysis gene, neither repressed by anaerobiosis nor by catabolic repression and strongly expressed during alcoholic fermentation, and (iv) deleting at least one copy or preferably at least two copies of the open reading frame (ORF) of the *Saccharomyces cerevisiae* GRE3 gene coding for an aldose reductase. Preferably, all copies of the open reading frame (ORF) of the *Saccharomyces cerevisiae* gene GRE3 gene are deleted.

The XKS1 gene is preferably the gene reported in GenBank under number 853108.

The GRE3 gene is preferably the gene reported in GenBank under number 856504.

Preferentially, the gene of step (ii)a is a gene XI coding for the xylose isomerase enzyme selected from those present in the genomes of the *Clostridium, Pyromyces, Bacteroides, Streptomyces, Haemophilus, Burkholderia, Enterococcus, Thermotoga, Fusobacterium, Geobacillus, Arthrobacter, Ciona, Physcomitrella, Cellvibrio, Chitinophaga, Saccharopolyspora, Salinibacter* genera.

The XI gene is preferably selected from a gene of *Clostridium phytofermentans, Saccharopolyspora erythraea, Salinibacter ruber* or *Piromyces* sp. E2.

According to a preferred embodiment, the sequence of the XI gene is the SEQ ID NO:1 nucleotide sequence (which corresponds to the sequence of the XI gene from *Clostridium phytofermentans*, described in document DE 102008031350). Alternatively, the XI gene has a sequence which has at least 70% identity, preferably at least 75% identity, or at least 80% identity, or at least 85% identity, or at least 90% identity, or at least 95% identity, or at least 98% identity, or at least 99% identity, with SEQ ID NO:1, and it codes for a functional xylose isomerase enzyme.

According to another embodiment, the XI gene has a sequence coding for a polypeptide having the amino acid sequence SEQ ID NO:2 (which corresponds to the sequence of the XI protein from *Clostridium phytofermentans* described in document DE 102008031350). Alternatively, said polypeptide has a sequence having at least 70% identity, preferably at least 75% identity, or at least 80% identity, or at least 85% identity, or at least 90% identity, or at least 95% identity, or at least 98% identity, or at least 99% identity, with SEQ ID NO:2 and it has a xylose isomerase activity.

According to the present invention by <<transforming any pentol into xylulose in a single step>> is meant direct oxidation of xylitol into xylulose and this by a same and single enzyme (xylitol dehydrogenase).

Preferentially, the gene of step (ii)b, is a *Pichia stipitis* gene coding for the xylitol dehydrogenase enzyme XDH. Preferably, it is the XYL2 gene, the sequence of which is the sequence reported in GenBank under number 4852013, or a sequence at least 70% identical, preferably at least 75% identical, or at least 80% identical, or at least 85% identical, or at least 90% identical, or at least 95% identical, or at least 98% oidentical, or at least 99% identical, to said sequence reported in GenBank under number 4852013, and coding for a functional xylitol dehydrogenase enzyme.

Preferentially, the yeast strain of step (i) has an endogenous xylitol dehydrogenase XDH activity of less than 150 mKat/g of proteins. The xylitol dehydrogenase activity can be measured in the conditions set forth in the article by Xu et al. entitled *Characterization of Ethanol Production from Xylose and Xylitol by a Cell-Free Pachysolen tannophilus System*, in Appl. Environ. Microbiol. 59:231-235 (1993).

It is known that during the processing of the biomass intended for alcoholic fermentation, certain fermentation inhibitors appear. Among them, mention may be made of phenolic products, of furfural or further acetic acid. It is also known that these inhibitors are detrimental for the performances or even the survival of the yeast.

In order to solve this additional problem, the Applicant suggests selecting the strain of step i, from industrial strains having resistance to phenolic derivatives.

Another advantage of the XI route, is the possibility of <<grafting the bacterial arabinose route in parallel>> as for example described in EP 1 499 708 or further in WO 2008/041840, this combination then allowing an increase in the final degree of alcohol in the case of the presence of arabinose in the media to be fermented.

The method for preparing the yeast of the present invention takes into account both the constraints of the yeast producer and at the same time those of a final user in its applications notably in terms of industrial production of ethanol with low cost and high yield.

The method according to the invention in particular has the following advantages:

For the yeast producer, it allows:
construction of a prototrophic aneu/polyploid, *Saccharomyces cerevisiae* yeast strain in order to allow production of biomass on simple sources of carbon, nitrogen, phosphorous in inexpensive media such as the byproducts of the sugar industry like molasses for example,
availability of a *Saccharomyces cerevisiae* yeast strain having a maximum growth rate (µ max) comprised between $0.37 \text{ h}^{-1}$ and $0.5 \text{ h}^{-1}$,
availability of a *Saccharomyces cerevisiae* yeast strain which, when it is produced according to a method as described in the reference book <<Yeast Technology>> (2nd edition, 1991, G. Reed and T. W. Nagodawithana, published by Van Nostrand Reinhold, ISBN 0-442-31892-8), gives the possibility of obtaining a biomass production yield of at least 45 g of yeast dry materials for 100 g of saccharose equivalent applied,
availability of a *Saccharomyces cerevisiae* yeast strain, resistant to the drying process as described in patent documents EP 511108 and U.S. Pat. No. 5,741,695, the loss of fermentative activity after drying should not exceed 30%,
production under industrial conditions (in particular, inexpensive medium, good biomass yield, dry ready-to-use yeast) of a fresh or dry yeast from a genetically stable, *Saccharomyces cerevisiae* yeast strain notably robust because it is tolerant to high concentrations of ethanol and capable of producing, for example from hemi-cellulose biomasses, at least 40 g/L of ethanol and this at a high temperature of the order of 30 to 40° C.

A prototrophic yeast strain is a strain capable of growing on a minimal medium. In particular, a prototrophic yeast strain according to the invention is capable of synthetizing all amino acids and bases that are necessary for its growth.

A minimal medium is a medium comprising a source of carbon, a source of nitrogen, a source of potassium, a source of phosphorus, a source of sulfur, a source of magnesium, a source of calcium, a source of iron, a source of trace elements and water.

An example of minimal medium is the YNB medium (Yeast Nitrogen Base). The YNB medium comprises, per liter: 2 µg biotin, 400 µg calcium pantothenate, 2 µg folic acid, 2000 µg inositol, 400 µg niacin, 200 µg p-aminobenzoic acid, 400 µg pyridoxine hydrochloride, 200 µg riboflavin, 400 µg thiamin hydrochloride, 500 µg boric acid, 40 µg copper sulfate, 100 µg potassium iodide, 200 µg ferric chloride, 400 µg manganese sulfate, 200 µg sodium molybdate, 400 µg zinc sulfate, 1 g monobasic potassium phosphate, 500 mg magnesium sulfate, 100 mg sodium chloride, 100 mg calcium chloride, 5 g ammonium sulfate, final pH 5.4.

According to another preferred alternative of the method according to the invention, when in step (ii) the expression cassette consists in the association of the open reading frame (ORF) type of the gene XI coding for the xylose isomerase enzyme of *Clostridium phytofermentans*/promoter and terminator of *Saccharomyces cerevisiae*, said cassette being flanked upstream and downstream with recombinogeneic regions allowing its targeted integration into the genome, said method then further includes a step for saccharification and simultaneous fermentation (SSF) in the presence of polymers of hexoses, in majority consisting of glucose, and of at least one enzyme capable of hydrolyzing them.

Moreover, for the ethanol producer, the advantage of the method according to the invention is further to have an active (fresh—liquid or compressed, pressed together or dry) yeast, obtained according to a production method as described in the textbook <<Yeast Technology>>, from a *Saccharomyces cerevisiae* yeast strain as defined in the preceding paragraph which is:
capable, under the SSF conditions described in patent document WO 2004/046333, of fermenting at 32° C. a hydrolyzate of cereals up to a minimum ethanol concentration of 16% (w/w),
capable, under the SSF conditions described in patent document WO 2004/046333, of fermenting at 35° C. a hydrolyzate of cereals up to a minimum ethanol concentration of 14.5% (w/w).

The results of the method according to the invention are all the more remarkable when they are obtained from a prototrophic aneu/polyploid so-called industrial strain and in fact having a clearly more complex genetic material than that of a so-called laboratory strain, at the very least making the consequences of modifications of said industrial strain unpredictable. This complex genetic background, specific to industrial strains, makes it all the more difficult to obtain genetically modified strains finally free of markers of resistance to antibiotics, in particular when many genetic targets have to be modified. Strains free of markers of resistance to antibiotics are quite obviously preferable for health and environment reasons.

The prototrophic strains according to the invention have the advantage of growing on simple sources of carbon, nitrogen and phosphorus.

But this feature causes the transformation vectors available in the scientific community (vectors using auxotrophy markers) to be inoperative.

It is therefore necessary to have available tools/vectors using markers of resistance to antibiotics, these so-called tools/markers being advantageously constructed in order to allow in fine excision of these markers. By way of example, use can be made of the Cre-lox technology. In brief, loxP sequences are provided on each side of each selection marker. Excision of the selection markers is performed by transforming the yeast strain by the lithium acetate method (Schiestl et Gietz, 1989, Current Genetics, vol 16, p. 339-346), using a plasmid comprising the Cre recombinase gene and a selection marker different from the selection marker(s) to be excised. The expression of the Cre recombinase in the yeast strain makes it possible to excise the selection marker, leaving only a loxP sequence, possibly together with its flanking sequences. It is then possible to induce the loss of the plasmid comprising the Cre gene by culturing in non-selective conditions, i.e. in an enriched medium in the absence of antibiotics. The construction of yeasts compliant with the invention for example required the use of 4 different positive markers giving resistances to 5 different antibiotics (geneticin, phleomycin, hygromycin, blasticidin and nourseothricin).

The strains compliant with the invention are preferably aneuploids or polyploids: this is a feature generally encountered in industrial yeasts which stem from the natural medium. The phylogenetic past of these strains is at the origin of this particularity.

But this is an additional difficulty encountered when it is desired to disrupt/inactivate all the copies of a given gene. However, this aneu/polyploidy feature is generally at the origin of many interesting properties of industrial yeasts (growth rate, resistance to different stresses, phenotype stability).

Further, the Applicant after long research work noticed surprisingly that with the method according to the invention, applied from the selected strain:
the introduction of expression and deletion cassettes by no means made the modified yeast fragile, which experiences improvement in its genetic heritage.

In particular, the inventors have shown that with said strain, it is possible to achieve:
the deletion of at least two copies of the gene GRE3 of S. cerevisiae (the Gre3P enzyme being an aldose reductase which consumes NADPH,H+ which is produced for a major part via the oxidative portion of the pentose route) in said industrial strain according to the invention allowed reduction in the consumption of NADPH,H+ by said enzyme, by that much.

As a preferred alternative, said at least one gene of each step of the non-oxidative portion of the phosphate pentose route of step (iii) is selected from the group formed by the genes coding for the D-ribulose-5-phosphate 3-epimerase, ribose-5-phosphate ketol-isomerase, transketolase and transaldolase enzymes, and notably from the group of the RPE1, RKI1, TKL1 and TAL1 genes. Preferably, said promoter of a strongly expressed glycolysis gene during alcoholic fermentation is the TDH3 promoter for RPE1, RKI1 and TKL1, and PGK1 for TAL1.

The TAL1 gene is preferably the gene reported in GenBank under number 851068.

The TKL1 gene is preferably the gene reported in GenBank under number 856188.

The RKI1 gene is preferably the gene reported in GenBank under number 854262.

The RPE1 gene is preferably the gene reported in GenBank under number 853322.

According to complementary or alternative features in the method for preparing a Saccharomyces cerevisiae yeast strain according to the invention:
the Saccharomyces cerevisiae promoter of steps (ii)(a) and (ii)(b) is selected from the group comprising the promoters of genes coding for glycolysis enzymes and those coding for the alcohol dehydrogenase enzymes and preferably selected from the group formed by ADH1, ADH2, PGK1, TDH3, PDC2 and GAL1/10, preferably ADH1. The terminator of Saccharomyces cerevisiae is formed by CYC1 or by the specific terminator of the gene of the non-oxidative pentose phosphate pathway.

Provision is preferably made for a subsequent directed evolution step including the following successive steps consisting of subjecting the obtained yeast to
(i) mutagenesis,
(ii) growth in cyclic cultures under limited $O_2$ in a medium including said at least one pentose, and
(iii) selection by aerobic growth on a solid medium containing glycerol as a single source of carbon,
so as to provide respiratory non-deficient mutants of said yeast which exhibit growth in anaerobiosis in the presence of a medium including said at least one pentose (notably xylose).

Preferably in this alternative, the mutagenesis of step (i) is performed under <<mild>> conditions, i.e. moderate mutagenesis with 100 to 500 $J/cm^2$ and still preferably 300 $J/cm^2$ of ultraviolet radiation at 254 nm. These conditions only cause mortality of 7% to 16% of the population subject to UVs.

The inventors have thereby shown surprisingly that with such a so low controlled mortality, it is possible to reduce by a factor 10 the duration of the directed evolution step with cyclic cultures required for obtaining mutants capable of fermenting said at least one pentose (notably xylose). The survival rate is determined by spreading out on medium dishes, the carbon source of which is glucose, an identical volume of the cell suspension before and after mutagenesis. The number of colonies is determined after 48 h of growth.

Preferably, the $O_2$ limitation of step (ii) of this alternative is achieved by partial overpressure in the equipments used (for example vials or fermenters) due to overpressure consecutive to production of produced $CO_2$.

The cyclic cultures according to this alternative, under fermentation conditions, give the possibility of enriching the population in mutants capable of fermenting said pentose (notably xylose) and this within a period from 2 to 6 weeks and preferably from 3 to 4 weeks which is relatively short and highly interesting as compared with what would be obtained by chemostat, as described by Kuyper et al. (2004), FEMS Yeast Res. 4, 655-664.

Although the <<petite>> respiratory deficient phenotype may coincide with the fermentation criteria of said at least one pentose, in this alternative, the present inventors carried out a step for removing <<petite>> yeasts since this phenotype is incompatible with the methods for producing industrial yeasts in the sense of the invention.

The searchers noted that the directed evolution step as explained above made it possible to significantly increase the xylose isomerase activity, which is characterized by an increase it the xylose consumption rate.

Without wishing to be bound by theory, this unexpected effect seems to be attributable to an increase in the number of XI copies in the modified strain.

The object of the present invention is further the EG6 Saccharomyces cerevisiae industrial yeast strain directly obtained by the method according to the invention after the step of directed evolution and which consists in the yeast strain deposited on Nov. 23, 2010 at the C.N.C.M (Collection Nationale de Cultures de Microorganismes of the Pasteur Institute, 25 rue du Docteur Roux, 75724 Paris, France) under No. I-4399 under the terms of the Budapest treaty.

The object of the present invention is also the EG7 Saccharomyces cerevisiae industrial yeast strain directly obtained by the method according to the invention after the directed evolution step, deposited on Nov. 23, 2010 at the C.N.C.M (Collection Nationale de Cultures de Microorganismes de l'Institut Pasteur) under No. I-4400 under the terms of the Budapest treaty.

The object of the present invention is also the EG8 *Saccharomyces cerevisiae* industrial yeast strain directly obtained by the method according to the invention after the directed evolution step, deposited on Dec. 14, 2010 at the C.N.C.M (Collection Nationale de Cultures de Microorganismes de l'Institut Pasteur) under No. I-4417 under the terms of the Budapest treaty.

The object of the present invention is also the EG10 *Saccharomyces cerevisiae* industrial yeast strain directly obtained by the method according to the invention after the directed evolution step, deposited on Oct. 5, 2011 at the C.N.C.M (Collection Nationale de Cultures de Microorganismes de l'Institut Pasteur) under No. I-4538 under the terms of the Budapest treaty.

Other strains according to the invention are strains derived from one or more strains according to the invention, for example from one or several strains obtained by the above method, and notably from one or more of the strains deposited at the CNCM under No. I-4399 on Nov. 23, 2010, under No. I-4400 on Nov. 23, 2010, under No. I-4417 on Dec. 14, 2010 and under No. I-4538 on Oct. 5, 2011.

By the expression "derived strain" is meant in particular strains derived by one or more cross-breedings and/or by mutation and/or by genetic transformation.

The strains derived by cross-breeding can be obtained by cross-breeding a strain according to the invention with the same strain, or with another strain according to the invention, or with any other strain.

The strains derived by mutation can be strains which have undergone at least one spontaneous mutation in their genome or at least one mutation induced by mutagenesis. The mutation(s) of the derived strains can be silent or not.

By "mutagenesis" is meant both random mutagenesis obtained by applying radiation (e.g. UV) or by mutagenic chemicals, and insertional or directed mutagenesis, by transposition or by integration of an exogenous DNA fragment.

The derived strains which are within the framework of the invention are those which comprise at least one exogenous XI gene and one exogenous XDH gene and which are capable of fermenting xylose to produce ethanol, and notably with an average yield of ethanol produced by consumed xylose greater than or equal to 0.2 g, preferably 0.3 g, 0.35 g or even 0.38 g ethanol per g of consumed xylose.

These derived strains also preferably exhibit a deletion of the GRE3 gene and/or a control of the XKS1 and/or RPE1 and/or RKI1 and/or TKL1 and/or TAL1 genes by a promoter of a gene which is not repressed by anaerobiosis or by catabolic repression induced by any source of carbon, and strongly expressed during alcoholic fermentation, such as a promoter of a gene coding for a glycolysis enzyme or coding for an alcohol dehydrogenase enzyme, preferably the ADH1, PGK1, TDH3, PDC2 or GAL1/10 promoter.

Still preferably,
the obtained *Saccharomyces cerevisiae* yeast strain is practically or totally free of markers notably of resistance to antibiotics.

Preferably, the *Saccharomyces cerevisiae* yeast strains prepared according to the present invention according to the criteria defined above retain, after introduction of the genetic modifications and other mutations generated during the directed evolution step, their genotype and phenotype characteristics after a complete industrial production process. In particular, the yeasts produced have kinetics for producing alcohol, kinetics for consuming xylose and/or arabinose and a maximum produced amount of alcohol, strictly identical with those of the yeast strain before applying a complete industrial process.

Moreover, the industrial characteristics of the selected strain before manipulation, as described earlier (growth rate, production yield, drying capacity) remain unchanged.

The object of the present invention is also a method for producing ethanol from a medium including at least one pentose, by fermentation with yeast according to the invention, mentioned above, or such as obtained with a method according to the invention as it has just been described.

Preferably, the method for producing ethanol has the following alternative and/or complementary characteristics:
Said at least one pentose is xylose or a mixture of xylose and arabinose.
Said medium is selected from the group formed by lignin, cellulose, hemi-cellulose dextrin or starch hydrolyzates.
In the case of an SSF, the average rates for releasing the hexose, in majority glucose, are of the order of 2.8 to 5.6 g/L/h with zero extracellular concentration of hexose, in majority glucose.
The average yield of ethanol produced by consumed xylose is greater than or equal to 0.38 g ethanol per g of consumed xylose, for example it can be approximately 0.40 g ethanol per g of consumed xylose.

The concentrations of sugars which can be applied (for example 70 g/kg of xylose or 150 g/kg of xylose) to the knowledge of the Applicant are the maximum concentrations which may be encountered in practice. All the published tests referring to fermentation of xylose were conducted with clearly lower concentrations of total sugars.

Other features and advantages of the invention will become still better apparent upon reading the exemplary embodiments which are given purely as an illustration and not as a limitation, and for the understanding of which reference will be made to the appended drawings.

EXAMPLES

Example 1

The selection of the strain is as described in the description above.

All the DNA sequences which were used for the different transformations aiming at overexpression of a gene were obtained from a known vector type (pUC type) in which are provided:
the integration targets;
the promoters/terminators selected per gene of interest and the resistance markers which will be removed subsequently (see below).

An exemplary vector used for overexpression of the XDH of *Pichia stipitis* is illustrated in FIG. 1.

Figure 2:
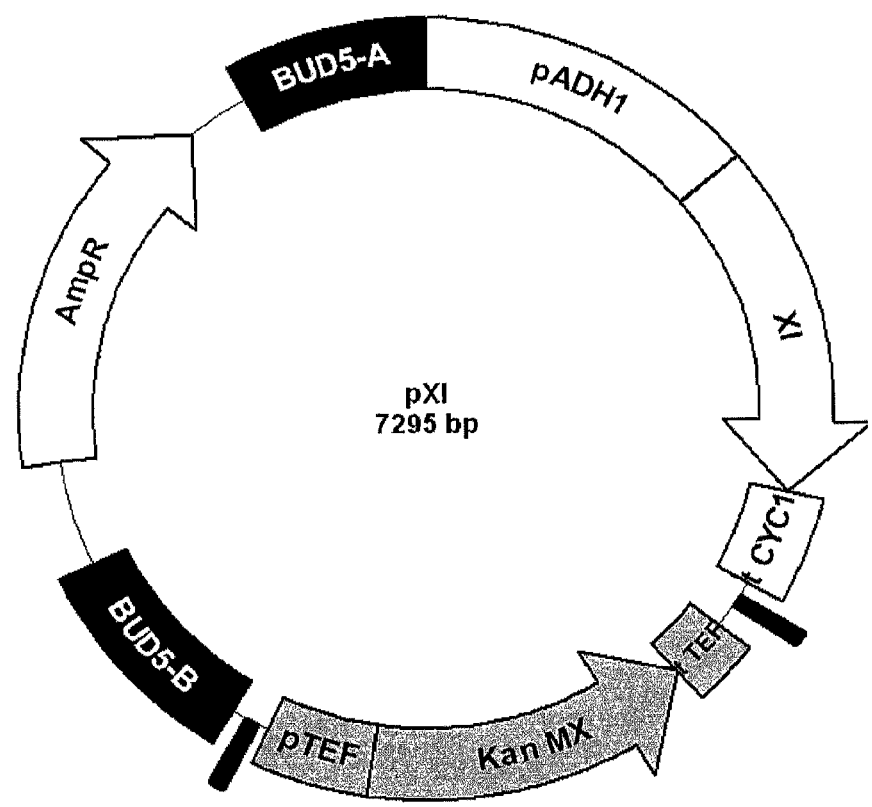
FIG. 2 illustrates an overexpression vector of XI from *Clostridium phytofermentans*.
Figure 3:
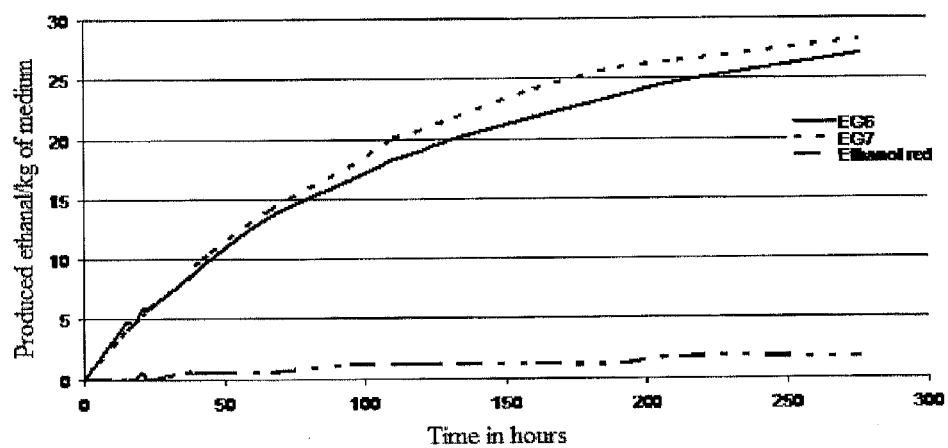
FIG. 3 is a graph illustrating the production of ethanol versus the fermentation time at 32° C. of two yeast strains according to the invention after directed evolution, and of the Ethanol Red™ strain. The tested clones were inoculated in an amount of 5 g of dry mass/L in a YF+70 g/L xylose medium.

An exemplary vector used for overexpression of the XI of *Clostridium phytofermentans* is illustrated in FIG. 2.

For disrupting the copies of the GRE3 gene of the selected industrial strain, the inventors used PCR amplificates from a plasmid of the pUG6 type (Güldener U, Heck S, Fielder T, Beinhauer J, Hegemann J H. Nucleic Acids Res. 1996 Jul. 1; 24(13):2519-24).

The step for transforming the yeast was applied according to Gietz, R. D. and R. A. Woods. (2002) TRANSFORMATION OF YEAST BY THE Liac/SS CARRIER DNA/PEG METHOD. Methods in Enzymology 350: 87-96.

The yeast strains according to the invention, EG6, EG7, EG8 and EG10 respectively, were deposited at the CNCM and No. I-4399, No. I-4400, No. I-4417 and No. I-4358 were respectively assigned to them.

The strains according to the invention:
have the following genotype:
Ethanol Red™, Delta GRE3, BUD5::pADH1-XKS1-tCYC1, TAL1::pPGK1-TAL1-tCYC1, TKL1::pTDH3-TKL1-tCYC1, RPE1::pTDH3-RPE1-tCYC1, RKI1::pTDH3-RKI1-tCYC1, HO::PsXYL2-HYGRO, BUD5::CpXI-BLAST
are free of any residual marker (by the action of cre recombinase).

Example 2

Mutagenesis of these strains obtained in the previous example was performed moderately i.e. from 100 to 500 J/cm$^2$ and preferably 300 J/cm$^2$ of UVs at 254 nm.

After a week of cultivation at 32° C. in a YE type medium (0.5% Yeast Extract) containing 7% of xylose, with stirring, without ventilation—the O$_2$ limitation being achieved by means of partial overpressure in the vials due to CO$_2$ produced during fermentation—one ml of the culture is used for resowing the same medium. This operation is repeated 6 times. The cells are finally spread out on a gelose YE 20 g/L glucose medium. Isolated colonies are sampled and then successively cultivated on:
- YE 20 g/L glycerol and in aerobiosis for removing the <<petite>> i.e. respiratory deficient mutants;
- YE glucose for checking their growth rate;
- YE xylose for identifying the most interesting clones.

Example 3

Figure 4:
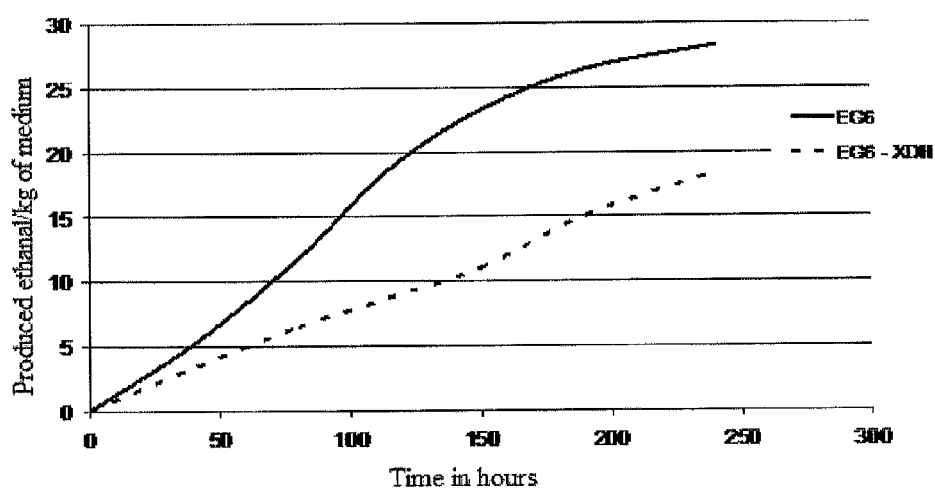
FIG. 4 is a graph illustrating the production of ethanol versus the fermentation time at 32° C. of two yeast strains, one according to the invention after directed evolution, the other strain resulting from the first one but after substitution of the copy of the XDH gene by a marker of resistance to kanamycin (KanMX4). The tested clones were inoculated in an amount of 5 g of dry mass/L in a YF+70 g/L xylose medium.
Figure 5:
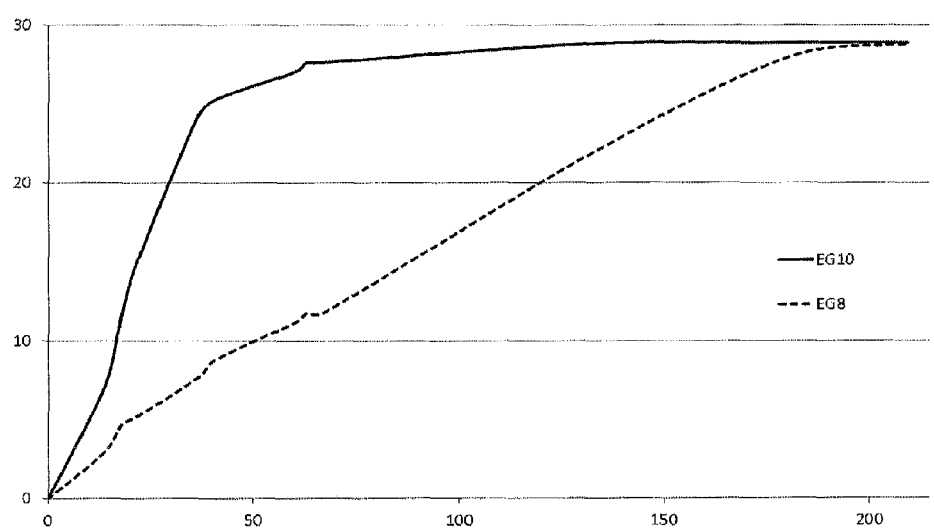
FIG. 5 is a graph illustrating the production of ethanol (Y-axis, in g per kg of medium) as a function of the fermentation time at 32° C. (X-axis, in hours) by two yeast strains according to the invention EG8 and EG10. The tested clones were inoculated at 0.25 g yeast dry matter per kg of YF medium containing 70 g/L xylose as the sole source of carbon.

After obtaining the EG6 strain, the copy of the XDH gene which was added to Example 1, was substituted with the gene of resistance to kanamycin. The new obtained strain is called EG6—XDH. The xylose fermenting capacity of the relevant strain was compared with that of the EG6 strain. The result of this comparison is shown in FIG. 4.

The invention claimed is:

1. A yeast strain comprising exogenous enzyme genes of the xylose metabolic pathway consisting of at least one copy of an exogenous gene encoding a xylose isomerase, and at least one copy of an exogenous gene encoding a xylitol dehydrogenase, wherein the exogenous gene encoding a xylose isomerase and the exogenous gene encoding a xylitol dehydrogenase are the only exogenous enzyme genes of the xylose metabolic pathway present in the yeast strain, and wherein the exogenous gene encoding a xylose isomerase is a gene from *Clostridium, Piromyces, Bacteroides, Streptomyces, Haemophilus, Burkholderia, Enterococcus, Thermotoga, Fusobacterium, Geobacillus, Arthrobacter, Ciona, Physcomitrella, Cellvibrio, Chitinophaga, Saccharopolyspora* or *Salinibacter*.

2. The yeast strain of claim 1, wherein the exogenous gene encoding a xylitol dehydrogenase is from *Pichia stipitis*.

3. The yeast strain of claim 1, wherein said strain is selected from *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp. et *Debaryomyces* spp.

4. A yeast strain according to claim 1, wherein at least copy of a gene encoding an aldose reductase is deleted.

5. The yeast strain of claim 4, wherein the deleted gene is GRE3.

6. The yeast strain of claim 1, wherein an endogenous gene encoding a xylulokinase, is placed under the control of a promoter of a gene which is not repressed by anaerobiosis or by catabolic repression induced by any source of carbon, and strongly expressed during alcoholic fermentation.

7. The yeast strain of claim 1, wherein at least one endogenous gene of the non-oxidative part of the pentose phosphate pathway is placed under the control of a promoter of a gene which is not repressed by anaerobiosis or by catabolic repression induced by any source of carbon, and strongly expressed during alcoholic fermentation.

8. The yeast strain of claim 7, wherein the promoter is a promoter of a gene coding for a glycolysis enzyme or coding for an alcohol dehydrogenase enzyme.

9. The yeast strain of claim 1, wherein said yeast strain is an aneuploid or polyploid strain and/or which is a prototrophic strain.

10. The yeast strain of claim 1, wherein said yeast strain comprises at least two copies of the exogenous gene encoding a xylose isomerase.

11. The yeast strain of claim 1, wherein said yeast strain is an industrial strain displaying resistance to fermentation inhibitors from the hydrolysis of biomass.

12. The yeast strain of claim 1, wherein said yeast strain produces an ethanol concentration of at least 16%, on a cereal hydrolyzate, in conditions of saccharification and simultaneous fermentation at 32° C.

13. The yeast strain of claim 1, wherein said yeast strain is selected from the group consisting of the *Saccharomyces cerevisiae* strain deposited at the CNCM on Nov. 23, 2010 under No. I-4399, the *Saccharomyces cerevisiae* strain deposited at the CNCM on Nov. 23, 2013 under No. I-4400, the *Saccharomyces cerevisiae* strain deposited at the CNCM on Dec. 14, 2010 under No. I-4417 and the *Saccharomyces cerevisiae* strain deposited at the CNCM on Oct. 5, 2011 under No. I-4538.

14. A yeast strain derived from at least one yeast strain of claim 13, wherein said derived yeast strain is obtained by cross-breeding, mutation and/or genetic transformation of the yeast strain of claim 13; wherein said derived yeast strain comprises exogenous enzyme genes of the xylose metabolic pathway consisting of at least one copy of an exogenous gene encoding a xylose isomerase, and at least one copy of an exogenous gene encoding a xylitol dehydrogenase, wherein the exogenous gene encoding a xylose isomerase and the exogenous gene encoding a xylitol dehydrogenase are the only exogenous enzyme genes of the xylose metabolic pathway present in the derived yeast strain; and wherein said derived yeast strain produces ethanol by fermenting xylose.

15. A yeast strain, wherein said strain is obtained by introducing in a starting yeast strain at least one copy of an exogenous gene encoding a xylose isomerase, and at least one copy of an exogenous gene encoding xylitol dehydrogenase, wherein the exogenous gene encoding a xylose isomerase and the exogenous gene encoding a xylitol dehydrogenase are the only exogenous enzymes genes of the xylose metabolic pathway to be introduced in the starting yeast strain, and wherein the exogenous gene encoding a xylose isomerase is a gene from *Clostridium, Piromyces, Bacteroides, Streytomyces, Haemophilus, Burkholderia, Enterococcus, Thermotoga, Fusobacterium, Geobacillm, Arthrobacter, Ciona, Physcomitrella, Cellvibrio, Chitinoyham, Saccharovolysvora* or *Salinibacter*.

16. The yeast strain of claim 1, wherein the exogenous gene encoding a xylose isomerase is a gene from *Clostridium phytofermentans* or *Piromyces* sp. E2.

17. The yeast strain of claim 3, wherein said yeast strain is a *Saccharomyces cerevisiae* strain.

18. The yeast strain of claim 4, wherein at least two copies of a gene encoding an aldose reductase are deleted.

19. The yeast strain of claim 6, wherein the endogenous gene encoding a xylulokinase is the gene XKS1.

20. The yeast strain of claim 7, wherein the at least one endogenous gene of the non-oxidative part of the pentose phosphate pathway is selected from the group consisting of genes RPE1, RKI1, TKL1 and TAL1, and any combination thereof.

21. The yeast strain of claim 8, wherein the promoter is selected from the group consisting of the ADH1, PGK1, TDH3, PDC2 and GAL1/10 promoters.

22. The yeast strain of claim 10, wherein said yeast strain comprises at least three or at least four copies of the exogenous gene encoding a xylose isomerase.

23. The yeast strain of claim 11, wherein the fermentation inhibitors are selected from phenolic products, furfural, acetic acid and any combination thereof.

24. The yeast strain of claim 12, wherein said yeast strain produces an ethanol concentration of at least 17% v/v on a cereal hydrolyzate, in conditions of saccharification and simultaneous fermentation at 32° C.

25. A method of preparing a yeast strain according to claim 1, comprising introducing in a starting yeast strain at least one copy of an exogenous gene coding for a xylose isomerase, and at least one copy of an exogenous gene coding for a xylitol dehydrogenase.

26. The method of claim 25, moreover comprising the deletion of at least one copy, preferably at least two copies, of a gene coding for an aldose reductase, preferably the GRE3 gene, in the starting strain.

27. A method for producing ethanol from a medium including at least one pentose, comprising a step of fermenting a yeast strain according to claim 1 in said medium.

28. The method of claim 25, characterized in that said at least one pentose is xylose or a mixture of xylose and arabinose.

29. The method of claim 27 characterized in that said medium is selected from the group formed by lignin, cellulose, hemi-cellulose, starch hydrolyzates.

30. The method of claim 27, characterized in that the produced average ethanol yield over consumed xylose is greater than or equal to 0.38 g of ethanol per g of consumed xylose.

* * * * *

SEQUENCE LISTING

<160> NUMBER OF SEQ ID NOS: 2

<210> SEQ ID NO 1
<211> LENGTH: 1317
<212> TYPE: DNA
<213> ORGANISM: Clostridium phytofermentans

<400> SEQUENCE: 1

```
atgaaaaatt actttccaaa tgttccagaa gtaaaatacg aaggcccaaa ttcaacgaat      60
ccatttgctt ttaaatatta tgacgcaaat aaagttgtag cgggtaaaac aatgaaagag     120
cactgtcgtt ttgcattatc ttggtggcat actctttgtg caggtggtgc tgatccattc     180
ggtgtaacaa ctatggatag aacctacgga aatatcacag atccaatgga acttgctaag     240
gcaaaagttg acgctggttt cgaattaatg actaaattag gaattgaatt cttctgtttc     300
catgacgcag atattgctcc agaaggtgat acttttgaag agtcaaagaa gaatcttttt     360
gaaatcgttg attacatcaa agagaagatg gatcagactg tatcaagtt attatggggt      420 actgctaata actttagtca tccaagattt atgcatggtg cttccacatc ttgcaacgca     480
gacgtatttg catatgctgc tgctaagatt aagaatgcat tagatgcaac aattaaatta     540
ggcggtaaag gttatgtatt ctggggtggt cgtgaaggtt atgaaacact tcttaataca     600
gatttaggac ttgagcttga taatatggct agacttatga agatggctgt agagtatggc     660
cgtgcaaatg gttttgatgg cgacttctat attgagccaa agccaaagga accaaccaag     720
catcaatatg attttgatac agcaaccgta cttgctttcc ttcgcaaata tggcttagaa     780
aaagatttca agatgaacat tgaagcaaac catgctactc ttgcaggtca tacctttgaa     840
catgaacttg caatggctag agttaatggt gcatttggtt ctgtagatgc aaaccagggt     900
gatccaaacc ttggatggga tacggatcaa ttcccaactg atgttcatag tgcaactctt     960
gcaatgcttg aagtacttaa ggctggtgga ttcactaacg gcggacttaa ctttgatgca    1020
aaggtaagac gtggttcctt cgaatttgat gatattgcat acgttatat tgcaggaatg    1080 gatacttttg cacttggttt aattaaggct gctgagatta tcgacgatgg tagaatcgca    1140
aaatttgtag atgatcgtta tgcaagctat aaaacaggaa ttggtaaagc aattgtggat    1200
ggaactacat ctcttgaaga attagagcag tatgttttaa cacatagtga accagtaatg    1260
cagagtggtc gtcaggaagt tcttgaaaca atcgtaaata atattttatt tagataa       1317
```

```
<210> SEQ ID NO 2
<211> LENGTH: 438
<212> TYPE: PRT
<213> ORGANISM: Clostridium phytofermentans

<400> SEQUENCE: 2

Met Lys Asn Tyr Phe Pro Asn Val Pro Glu Val Lys Tyr Glu Gly Pro
1               5                   10                  15

Asn Ser Thr Asn Pro Phe Ala Phe Lys Tyr Tyr Asp Ala Asn Lys Val
            20                  25                  30

Val Ala Gly Lys Thr Met Lys Glu His Cys Arg Phe Ala Leu Ser Trp
        35                  40                  45

Trp His Thr Leu Cys Ala Gly Gly Ala Asp Pro Phe Gly Val Thr Thr
    50                  55                  60

Met Asp Arg Thr Tyr Gly Asn Ile Thr Asp Pro Met Glu Leu Ala Lys
65                  70                  75                  80

Ala Lys Val Asp Ala Gly Phe Glu Leu Met Thr Lys Leu Gly Ile Glu
                85                  90                  95

Phe Phe Cys Phe His Asp Ala Asp Ile Ala Pro Glu Gly Asp Thr Phe
            100                 105                 110

Glu Glu Ser Lys Lys Asn Leu Phe Glu Ile Val Asp Tyr Ile Lys Glu
        115                 120                 125

Lys Met Asp Gln Thr Gly Ile Lys Leu Leu Trp Gly Thr Ala Asn Asn
130                 135                 140

Phe Ser His Pro Arg Phe Met His Gly Ala Ser Thr Ser Cys Asn Ala
145                 150                 155                 160

Asp Val Phe Ala Tyr Ala Ala Ala Lys Ile Lys Asn Ala Leu Asp Ala
                165                 170                 175

Thr Ile Lys Leu Gly Gly Lys Gly Tyr Val Phe Trp Gly Gly Arg Glu
            180                 185                 190

Gly Tyr Glu Thr Leu Leu Asn Thr Asp Leu Gly Leu Glu Leu Asp Asn
        195                 200                 205

Met Ala Arg Leu Met Lys Met Ala Val Glu Tyr Gly Arg Ala Asn Gly
210                 215                 220

Phe Asp Gly Asp Phe Tyr Ile Glu Pro Lys Pro Lys Gly Pro Thr Lys
225                 230                 235                 240

His Gln Tyr Asp Phe Asp Thr Ala Thr Val Leu Ala Phe Leu Arg Lys
                245                 250                 255

Tyr Gly Leu Glu Lys Asp Phe Lys Met Asn Ile Glu Ala Asn His Ala
            260                 265                 270

Thr Leu Ala Gly His Thr Phe Glu His Glu Leu Ala Met Ala Arg Val
        275                 280                 285

Asn Gly Ala Phe Gly Ser Val Asp Ala Asn Gln Gly Asp Pro Asn Leu
290                 295                 300

Gly Trp Asp Thr Asp Gln Phe Pro Thr Asp Val His Ser Ala Thr Leu
305                 310                 315                 320

Ala Met Leu Glu Val Leu Lys Ala Gly Gly Phe Thr Asn Gly Gly Leu
                325                 330                 335

Asn Phe Asp Ala Lys Val Arg Arg Gly Ser Phe Glu Phe Asp Asp Ile
            340                 345                 350

Ala Tyr Gly Tyr Ile Ala Gly Met Asp Thr Phe Ala Leu Gly Leu Ile
        355                 360                 365

Lys Ala Ala Glu Ile Ile Asp Asp Gly Arg Ile Ala Lys Phe Val Asp
370                 375                 380
```

-continued

```
Asp Arg Tyr Ala Ser Tyr Lys Thr Gly Ile Gly Lys Ala Ile Val Asp
385                 390                 395                 400

Gly Thr Thr Ser Leu Glu Glu Leu Glu Gln Tyr Val Leu Thr His Ser
                405                 410                 415

Glu Pro Val Met Gln Ser Gly Arg Gln Glu Val Leu Glu Thr Ile Val
                420                 425                 430

Asn Asn Ile Leu Phe Arg
            435
```